US006300475B1

(12) United States Patent
Chen et al.

(10) Patent No.: US 6,300,475 B1
(45) Date of Patent: *Oct. 9, 2001

(54) INTERFERON PRO655

(75) Inventors: Jian Chen, Plainsboro, NJ (US); William I. Wood, Hillsborough, CA (US)

(73) Assignee: Genentech, Inc., So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/206,936

(22) Filed: Dec. 7, 1998

Related U.S. Application Data
(60) Provisional application No. 60/067,897, filed on Dec. 8, 1997.

(51) Int. Cl.$^7$ .......................... C07K 14/00; C12P 21/04; C12N 15/09; C12N 15/63; C12N 5/00

(52) U.S. Cl. ................. 530/351; 530/350; 435/69.51; 435/320.1; 435/325; 435/252.3; 435/358; 435/254.2; 435/252.33; 435/254.11; 536/23.5; 536/23.1; 536/23.52

(58) Field of Search ....................... 536/23.5; 530/350, 530/351; 435/69.51, 320.1, 325, 252.3, 358, 254.2, 252.33, 254.11

(56) References Cited

U.S. PATENT DOCUMENTS

| 4,423,147 | 12/1983 | Secher et al. . |
|---|---|---|

FOREIGN PATENT DOCUMENTS

| 307247 | 3/1989 | (EP) . |
|---|---|---|
| 032134 B2 | 10/1993 | (EP) . |
| 2079291 | 1/1982 | (GB) . |
| 2123835 | 2/1984 | (GB) . |
| 2161270 | 1/1986 | (GB) . |
| 2161487 | 1/1986 | (GB) . |
| WO 93/04699 | 3/1993 | (WO) . |

OTHER PUBLICATIONS

Adams et al., "Use of a random human BAC end sequence database for sequence–ready map building" (EMBL Database Entry Accession No. AQ111637) (Sep. 4, 1998).
Alkan and Braun, "Epitope mapping of human recombinant interferon alpha molecules by monoclonal antibodies" *Synthetic peptides as antigens—Ciba Foundation Symposium 119* 119:264–278 (1986).
Barasoain et al., "Antibodies against a peptide representative of a conserved region of human IFN–α. Differential effects on the antiviral and proliferative effects of IFN" *Journal of Immunology* 143(2):507–512 (Jul. 15, 1989).
Baron et al., "From cloning to a commercial realization: human alpha interferon" *Crit. Rev. Biotech.* 10(3):179–190 (1990).
Bolivar et al., "Construction and Characterization of New Cloning Vehicles. II. A Multipurpose Cloning System" *Gene* 2:95–113 (1977).
Capon et al., "Designing CD4 Immunoadhesins for AIDS Therapy" *Nature* 337:525–531 (Feb. 9, 1989).
Capon et al., "Two distinct families of human and bovine interferon–α genes are coordinately expressed and encode functional polypeptides" *Molecular & Cellular Biology* 5:768–779 (1985).
Dafny et al., "Interferon modulates neuronal activity recorded from the hypothalamus, thalamus, hippocampus, amygdala and the somatosensory cortex" *Brain Research* 734(1–2):269–274 (Sep. 23, 1996).
Darnell et al., "Jak–STAT Pathways and Transcriptional Activation in Response to IFNs and Other Extracellular Signaling Proteins" *Science* 264(5164):1415–1421 (1994).
De Boer et al., "Construction of a tandem trp–lac promoter and a hybrid trp–lac promoter for efficient and controlled expression of the human growth hormone gene in *Escherichia coli*" *Promoter Structure and Function,* Rodriguez et al., New York:Praeger Publishers, Chapter 29, pp. 462–481 (1982).
De Maeyer and De Maeyer–Guignard, "Interferons" *The Cytokine Handbook,* 2nd edition, Chapter 15, pp. 265–288 (1994).
De Maeyer, E., "The Presence and Possible Pathogenic Role of Interferons in Disease" *Interferons and other Regulatory Cytokines,* John Wiley and Sons Publishers, Chapter 16, pp. 380–424 (1988).
Duarte et al., "Anticuerpos monoclonales de raton contra el interferon recombinants alfa 2. Su empleo en la purificacion y detection del antigeno" *Interferon y Biotechnologia* (An English language summary appears on the front page of the article) 4(3):221–232 (1987).
Evinger and Pestka, "Assay of growth inhibiton in lymphoblastoid cell cultures" *Methods in Enzymology* 79 (Pt B):362–368 (1981).
Exley et al., "A comparison of the neutralizing properties of monoclonal and polyclonal antibodies to human interferon alpha" *Journal of General Virology* 65:2277–2280 (1984).
Farkkila et al., "Clinical spectrum of neurological herpes simplex infection" *Acta Neurologica Scandinavica* 87(4):325–328 (1993).
Feng et al., "Progressive Alignment and Phylogenetic Tree Construction of Protein Sequences" *Methods in Enzymology* 183:375–387 (1990).
Gibbs et al., "A negative regulatory region in the intracellular domain of the human interferon–α receptor" *Journal of Biological Chemistry* 271(45):28710–28716 (Nov. 8, 1996).

(List continued on next page.)

*Primary Examiner*—Elizabeth Kemmerer
*Assistant Examiner*—Janet L. Andres
(74) *Attorney, Agent, or Firm*—Atulya R. Agarwal

(57) ABSTRACT

The invention concerns a human interferon, designated PRO655, and its variants and derivatives. The interferon is related to but distinct from members of the IFN-α family and from IFNs-β and -γ. Nucleic acid encoding the polypeptide, and methods and means for their recombinant production are also included.

15 Claims, 8 Drawing Sheets

OTHER PUBLICATIONS

Goeddel et al., "Human Leukocyte Interferon Produced by *E. coli* is Biologically Active" *Nature* 287(5781):411–416 (Oct. 2, 1980).

Goeddel et al., "Synthesis of Human Fibroblast Interferon by *E. coli*" *Nucleic Acids Research* 8(18):4057–4074 (1980).

Goeddel et al., "The structure of eight distinct cloned human leukocyte interferon cDNAs" *Nature* 290:20–26 (1981).

Gray et al., "Expression of Human Immune Interferon cDNA in *E. coli* and Monkey Cells" *Nature* 295:503–508 (Feb. 11, 1982).

Heidemann et al., "Gunstigerer verlauf des herpes zoster bei immunsupprimierten patienten unter behandlung mit fibroblasteninterferon" *Onkologie* (An English language summary appears on the front page of the article) 7:210–212 (1984).

Hertzog et al., "Neutralization of interferon α4 by a monoclonal antibody which blocks signal transduction" *Journal of Interferon Research* (abstract #119–15) 10(Suppl. 1):5170 (1990).

Holmes et al., "Structure and Functional Expression of a Human Interleukin–8 Receptor" *Science* 253(5025):1278–1280 (Sep. 13, 1991).

Knobler et al., "Systemic alpha–interferon therapy of multiple sclerosis" *Neurology* 34:1273–1279 (Oct. 1984).

Knoll and Lichter, "In situ hybridization and detection using nonisotropic probes" *Current Protocols in Molecular Biology* (Unit 14.7.1–14.7.14), Ausubel et al., New York:John Wiley & Sons (1995).

Knoll and Lichter, "In situ hybridization to metaphase chromosomes and interphase nuclei" *Current Protocols in Human Genetics* (Units 4.3.1–4.3.28), Dracopoli et al., New York:John Wiley & Sons vol. 1, (1995).

Kontsek et al., "Distinct effect of pH 2 on a common antigenic structure found in human interferons–$\alpha_1$ and –$\alpha_2$ in the region 30–35" *Journal of Interferon Research* 11:327–332 (1991).

"Labeling and colorimetric detection of nonisotropic probes" *Current Protocols in Molecular Biology* (Unit 3.18), Ausubel et al., New York:John Wiley & Sons pp. 3–42 – 3–46 (1997).

Lawn et al., "DNA sequence of two closely linked human leukocyte interferon genes" *Science* 212(4499):1159–1162 (Jun. 5, 1981).

Levy et al., "Cytoplasmic Activation of ISGF3, the Positive Regulator of Interferon–α–Stimulated Transcription, Reconstituted In Vitro" *Genes & Development* 3:1362–1371 (1989).

Lu et al., "Structure–function study of the extracellular domain of the human IFN–α receptor (hIFNAR1) using blocking monoclonal antibodies: the role of domains 1 and 2" *Journal of Immunology* 160(4):1782–1788 (Feb. 15, 1998).

Lund et al., "Novel cluster of α–interferon gene sequences in a placental cosmid DNA library" *Proc. Natl. Acad. Sci. USA* 81(8):2435–2439 (Apr. 1984).

Merigan et al., "Human leukocyte interferon for the treatment of herpes zoster in patients with cancer" *N. Engl. J. Med* 298(18):981–987 (May 4, 1978).

Morehead et al., "Roles of the 29–138 disulfide bond of subtype A of human α interferon in its antiviral activity and conformational stability" *Biochemistry* 23(11):2500–2507 (May 22, 1984).

Nagata et al., "Synthesis in *E. coli* of a polypeptide with human leukocyte interferon activity" *Nature* 284(5754):316–320 (1980).

Nagata et al., "The structure of one of the eight or more distinct chromosomal genes for human interferon–α" *Nature* 287 (5781):401–408 (Oct. 2, 1980).

Noll et al., "Production and characterization of four monoclonal antibodies specific for human interferon–alpha–1 and –alpha–2" *Biomedica Biochemica Acta* 48(1):165–176 (1989).

Novick et al., "The human interferon α/β receptor: characterization and molecular cloning" *Cell* 77:391–400 (1994).

Pestka, S., "The human interferon–α species and hybrid proteins" *Seminars in Oncology* 24(3 Supp.9):S9–4 –S9–17 (Jun. 1997).

Pestka, S., "The human interferons—from protein purification and sequence to cloning and expression in bacteria: before, between, and beyond" *Archives of Biochemistry & Biophysics* 221(1):1–37 (Feb. 15, 1983).

Pfeffer, L., "Biologic activities of natural and synthetic type I interferons" *Seminars in Oncology* 24(3 Suppl 9):S9–63 – S9–69 (Jun. 1997).

Picken et al., "Nucleotide sequence of the gene for heat–stable enterotoxin II of *Escherichia coli*" *Infection and Immunity* 42(1):269–275 (1983).

Plioplys and Massimini, "Alpha/beta interferon is a neuronal growth factor" *Neuroimmunomodulation* 2(1):31–35 (Jan.–Feb. 1995).

Reis et al., "Antigenic characterization of human interferon derived from amniotic membranes induced by virus" *Journal of Interferon Research* 9(5):573–581 (Oct. 1989).

Rubinstein et al., "Convenient assay for interferons" *Journal of Virology* 37(2):755–758 (Feb. 1981).

Ruppert et al., "Cloning and Expression of Human $TAF_{II}250$: a TBP–associated Factor Implicated in Cell–cycle Regulation" *Nature* 362:175–179 (1993).

Scholtissek et al., "A cloning cartridge of λ $t_o$ terminator" *Nucl. Acids Res.* 15(7):3185 (1987).

Shearer et al., "Monoclonal antibodies that distinguish between subspecies of human interferon–α and that detect interferon oligomers" *Journal of Immunology* 133(6):3096–3101 (Dec. 1984).

Sompayrac et al., "Efficient infection of monkey cells with DNA of simian virus 40" *Proc. Natl. Acad. Sci. USA* 78(12):7575–7578 (Dec. 1981).

Stancek et al., "Interferon–neutralizing or enhancing activities in hybridoma cell fluids after in vitro immunization" *Acta Virologica* 36(4):376–382 (Aug. 1992).

Streuli et al., "At least three human type α interferons: structure of α2" *Science* 209(4463):1343–1347 (Sep. 19, 1980).

Taniguchi et al., "Human leukocyte and fibroblast interferons are structurally related" *Nature* 285:547–549 (1980).

Thimmappaya et al., "Adenovirus VAI RNA is required for efficient translation of viral mRNAs at late times after infection" *Cell* 31(3 Pt 2):543–551 (Dec. 1982).

Tsukui et al., "A monclonal antibody with broad reactivity to human interferon–α subtypes useful for purification of leukocyte–derived interferon" *Microbiology & Immunology* 30(11):1129–1139 (1986).

Ullrich et al., "Nucleotides sequence of a portion of human chromosome 9 containing a leukocyte interferon gene cluster" *Journal of Molecular Biology* 156(3):467–486 (Apr. 15, 1982).

Uze et al., "Genetic transfer of a functional human interferon α receptor into mouse cells: cloning and expression of its cDNA" *Cell* 60:225–234 (1990).

Weissmann et al., "Structure and expression of human IFN–α genes" *Philosophical Transactions of the Royal Society of London—Series B: Biological Sciences* 299(1094):7–28 (Sep. 24, 1982).

Wetzel, R., "Assignment of the disulphide bonds of leukocyte interferon" *Nature* 289(5798):606–607 (Feb. 12, 1981).

Whaley et al., "Identification and cellular localization of unique interferon mRNA from human placenta" *Journal of Biological Chemistry* 269(14):10864–10868 (Apr. 8, 1994).

Zhang et al., "Neuregulin–3 (NRG3): A novel neural tissue–enriched protein that binds and activates ErbB4" *Proc. Natl. Acad. Sci. USA* 94:9562–9567 (Sep. 22, 1997).

Zhang et al., "STAT3 participates in transcriptional activation of the C–reactive protein gene by interleukin–6" *Journal of Biological Chemistry* 271(16):9503–9509 (Apr. 19, 1996).

<208 208 residues, 0 stop; molecular weight: 24414.41

```
      1       10        20        30        40        50        60        70
      |       |         |         |         |         |         |         |
      MIKHFFGTVLVLLASTTIFSLDLKLIIFQQRQVNQESLKLLNKLQTLSIQQCLPHRKNFLLPQKSLSPQ 71       80        90        100       110       120       130       140
      |       |         |         |         |         |         |         |
      QYQKGHTLAILHEMLQQIFSLFRANISLDGWEENHTEKFLIQLHQQLEYLEALMGLEAEKLSGTLGSDNL 141       150       160       170       180       190       200
      |       |         |         |         |         |         |
      RLQVKMYFRRIHDYLENQDYSTCAWAIVQVEISRCLFFVFSLTEKLSKQGRPLNDMKQELTTEFRSPR
``` v v v          v v              v v

FIG. 1

DNA50960

```
CTTAGATATTAAACTGATAGGATAAGATATAAAATAATTTAAGATTGCTGATATATGTTT
TAAAATTAATTATTTGCTCAAGCATTGTGACAATTTACAGTTCTCAATTGAGTTTAAA
TTTAGTAGTTGTAGGTATTTAAGTTTTGCCCCTGAATTCTTTATAGTGCTGATAAGC
CTTTGGTTAAGTTTTACTCCATGAAAGACTATTACTGAAAAAATGTAATCTCAATAAAA
GAACTTTAATAAGCTTGACTAAATAATTTAGAAAGCACATTGTGTTCAGTGAAACTTGTA
TATAATGAATAGAATAATAAAAGATTATGTTGGATGACTAGTCTGTAATTGCCTCAAGA
AGCCATAACAATGAATAAGTTATTTTGGTACTTCCTCAAAATGCCAACACACAATAGGAAA
TGGAGAAAAAGTACTCTGAACACCATGAAACCTGAAAATCTAATGTGTAAACTT
GGAGAAATGACATTAGAAACGAAAGCAACAAAAGAGAACACTCTCCAAATAATCTGAG
ATGCATGAAAGGCAAACATTCACTAGAGCTGGAATTTCCCTAAGTCTATGCAGGATAAG
TAGCATATATTTGACCTTCACC
><Met (trans=1-s, dir=f, res=1)>
ATGATTATCAAGCACTTCTTTGGAACTGTGTTGGTCGTGCCTCGGCCTCTACCACTATCTTC
TCTCTAGATTTGAAACTGATTATCTTCCAGCAAGAAGTGAATCAAGAAGTTTAAAA
CTCTGAATAAGTTGCAAACCTTGTCAATTCAGCAGTGTCTACCACAGAGAAAAACTTT
CTGCTTCCTCAGAAGTCTTGAGTCCTTGAGTCCTGAGCAGTACCAAAAGGACACACTCTGGCCATT
CTCCATGAGATGCTTCAGCAGATCTTCAGCCTCTTCAGGGCAAATATTCTCTGGATGGT
TGGGAGGAAAACCACAGGAGAATTCCTCATTCAACTTCATCAACAGCTAGAATACCTA
GAAGCACTCATGGGACTGAAGCAGAGAAGCTAAGTGTACTTTGGGTAGTGATAACCTT
AGATTACAAGTTAAAATGTACTTCCGAAGGATCCATGATTACCTGAAAACCAGGACTAC
AGCACCTGTGCCTGGGCCATTGCCAAATGAGCAAAACTGAGCAAGAAGACCCTGAACGACATGAAGCAAGAGCTT
AGTCTCACAGAGAATTTAGAGCCCGAGGTAGGTGGAGGACTAGAGGACTTCTCCAGACATGAT
ACTACAGAGTTTAGAGCCCGAGGTAGGTGGAGGACTAGAGGACTTCTCCAGACATGAT
TCTTCATAGAGTGGTAATACAATTATAGTACAATCACATTGCTTTGATTTGTGTATAT
ATATATTTATCTCAGTTTATCCATTTAAGATTGTCATATTGTATGTCAAATAAAATTCATTAAT
GTGGCTTTATATATTCTATCCATTTAAGATTGTCATATTGTATGTCAAATAAATTCATTAATA
TGGTTGATTCTTCAAAAAAAAAAAAAAAAAAAAAA
```

```
1001  AGCAGAGAAG CTAAGTGGTA CTTTGGGTAG TGATAACCTT AGATTACAAG TTAAAATGTA CTTCCGAAGG ATCCATGATT ACCTGGAAAA CCAGGACTAC
      TCGTCTCTTC GATTCACCAT GAAACCCATC ACTATTGGAA TCTAATGTTC AATTTTACAT GAAGGCTTCC TAGGTACTAA TGGACCTTTT GGTCCTGATG
 128   A  E  K   L  S  G    L  G  S    D  N  L    R  L  Q    K  N  Y    F  R  R    I  H  D  Y    L  E  N    Q  D  Y

1101  AGCACCTGTG CCTGGGCCAT TGTCCAAGTA GAAATCAGCC CTTTGTGTTC AGTCTCACAG AAAAACTGAG CAAACAAGGA AGACCCTTGA
      TCGTGGACAC GGACCCGGTA ACAGGTTCAT CTTTAGTCGG GAAACACAAG TCAGAGTGTC TTTTTGACTC GTTTGTTCCT TCTGGGAACT
 161   S  T  C   A  W  A  I    V  Q  V   E  I  S    R  L  F    V  S    L  T  E    K  L  S    K  Q  G    R  P  L  N

1201  ACGACATGAA GCAAGAGCTT ACTACAGAGT TTAGAAGCCC GAGGTAGGTG AGGACTTCTC CAGACATGAT TCTTCATAGA GTGGTAATAC
      TGCTGTACTT CGTTCTCGAA TGATGTCTCA AATCTTCGGG CTCCATCCAC TCCTGAAGAG GTCTGTACTA AGAAGTATCT CACCATTATG
 195   D  N  K    Q  E  L    T  T  E  F    R  S  P    R  S  P    R  T  S    D  M  I    L  H  R

1301  AATTTATAGT ACAATCACAT TGCTTTGATT ATATATTTAT CTGAGTTTTA AGATTGTGCA TATTGACCAC AATTGTTTTT
      TTAAATATCA TGTTAGTGTA ACGAAACTAA TATATAAATA GACTCAAAAT TCTAACACGT ATAACTGGTG TTAACAAAAA

1401  GTGGCTTTAT ATATTCTATC CATTTTAAAT TGTTTGTATG TCAAAAATAA TTCATTAATA TGGTTGATTC TCAAAAAAAA AAAAAAAAAA
      CACCGAAATA TATAAGATAG GTAAAATTTA ACAAACATAC AGTTTTATTT ATTTATTAAT AAGTAATTAT ACCAACTAAG AGTTTTTTTT TTTTTTTTTT

```
  1   AAACTTTCTG CTTCCTCAGA AGTCTTTGAG TCCTCAGCAG TACCAAAAAG GACACACTCT GGCCATTCTC CATGAGATGC
      TTTGAAAGAC GAAGGAGTCT TCAGAAACTC AGGAGTCGTC ATGGTTTTTC CTGTGTGAGA CCGGTAAGAG GTACTCTACG
  1     N F L   L P Q K   S L S   P Q Q   Y Q K G   H T L   A I L   H E M L
                                                              ^49668.p1

81   TTCAGGAGAT CTTCAGCCTC TTCAGGGCAA ATATTTCTCT GGATGGTTGG GAGGAAAACC ACACGGAGAA ATTCCTCATT
      AAGTCCTCTA GAAGTCGGAG AAGTCCCGTT TATAAAGAGA CCTACCAACC CTCCTTTTGG TGTGCCTCTT TAAGGAGTAA
 28     Q Q I   F S L   F R A N   I S L   D G W   E E N H   T E K   F L I

161   CAGCTTCATC AACAGCTAGA ATACCTAGAA GCACTCATGG GACTGGAAGC AGAGAAGCTA AGTGGTACTT TGGGTAGTGA
      GTNGAAGTAG TTGTCGATCT TATGGATCTT CGTGAGTACC CTGACCTTCG TCTCTTCGAT TCACCATGAA ACCCATCACT
 54     X L H Q   L E Y   L E   A L M G   L E A   E K L   S G T L   G S D
                                          ^49668.r2   ^49668.r1

241   TAACCTTAGA TTACAAGTTA AAATGTACTT CCGAAG
      ATTGGAATCT AATGTTCAAT TTTACATGAA GGCTTC
 81     N L R   L Q V K   M Y F R
```

FIG. 6

INTERFERON PRO655

This is a provisional application No. 60/067,897 filed Dec. 8, 1997, the entire disclosure of which is hereby incorporated by reference and to which application(s) priority is claimed under 35 USC §119.

FIELD OF THE INVENTION

The present invention relates generally to the identification and isolation of novel DNA and to the recombinant production of a novel member of the family of human interferons.

BACKGROUND OF THE INVENTION

Interferons are relatively small, single-chain glycoproteins released by cells invaded by viruses or certain other substances. Interferons are presently grouped into three major classes, designated leukocyte interferon (interferon-alpha, α-interferon, IFN-α), fibroblast interferon (interferon-beta, β-interferon, IFN-β), and immune interferon (interferon-gamma, γ-interferon, IFN-γ). In response to viral infection, lymphocytes synthesize primarily α-interferon (along with a lesser amount of a distinct interferon species, commonly referred to as omega interferon), while infection of fibroblasts usually induces β-interferon. α- and β-interferons share about 20–30 percent amino acid sequence homology. Thus, the gene for human IFN-β lacks introns, and encodes a protein possessing 29 % amino acid sequence identity with human IFNαI, suggesting that IFN-α and IFN-β genes have evolved from a common ancestor (Taniguchi et al., *Nature* 285, 547–549 (1980)). By contrast, IFN-γ is not induced by viral infection, rather, is synthesized by lymphocytesin response to mitogens, and is scarcely related to the other two types of interferons in amino acid sequence. Interferons-α and -β are known to induce MHC Class I antigens, while IFN-α induces MHC Class I antigen expression.

A large number of distinct genes encoding different species of IFNs-α have been identified. Alpha interferon species identified previously fall into two major classes, I and II, each containing a plurality of discrete proteins (Baron et al., *Critical Reviews in Biotechnology* 10, 179–190 (1990); Nagata et al., *Nature* 287, 401–408 (1980); Nagata et al., *Nature* 284, 316–320 (1980); Streuli et al, *Science* 209, 1343–1347 Goeddel et al., *Nature* 290, 20–26 (1981); Lawn et al., *Science* 212, 1159–1162 (1981); Ullrich et al., *J. Mol Biol.* 156, 467–486 (1982); Weissmann et al., *Phil. Trans. R. Soc. Lond. B* 299, 7–28 (1982); Lund et al., *Proc. Natl. Acad. Sci.* 81, 2435–2439 (1984); Capon et al., *Mol. Cell. Biol.* 5, 768 (1985)). The various IFN-α species include IFN-αA (IFN-α2), IFN-αB, IFN-αC, IFN-αC1, IFN-αD (IFN-α1), IFN-αE, IFN-αF, IFN-αG, IFN-αH, IFN-αI, IFN-αJ1, IFNαJ2, IFN-αK, IFN-αL, IFN-α4B, IFN-α5, IFN-α6, IFN-α74, IFN-a76 IFNα4a) IFN-α88, and alleles of these species. Interestingly, while only a single human IFN-α gene has been unequivocally identified, bovine IFN-β is encoded by a family of five or more homologous, yet distinct genes.

Interferons were originally produced from natural sources, such as buffy coat leukocytes and fibroblast cells, optionally using known inducing agents to increase interferon production. Interferons have also been produced by recombinant DNA technology.

The cloning and expression of recombinant IFN-αA (rIFN-αA) was described by Goeddel et al., *Nature* 287, 411 (1980). The amino acid sequences of rIFNs-αA, B, C, D, F, G, H, K and L, along with the encoding nucleotide sequences, are described by Pestka in *Archiv. Biochem. Biophys.* 221, 1 (1983). The amino acid sequences and the underlying nucleotide sequences of rIFNs-αE, I and J are described in British Patent Specification No. 2,079,291, published Jan. 20, 1982. Hybrids of various IFNs-α are also known, and are disclosed, e.g. by Pestka et al., supra. Nagata et al., *Nature* 284, 316 (1980), described the expression of an IFN-α gene, which encoded a polypeptide (in non-mature form) that differs from rIFN-αD by a single amino acid at position 114. Similarly, the cloning and expression of an IFN-α gene (designated as rIFN-α2) yielding a polypeptide differing from rIFN-αA by a single amino acid at position23, was described in European Patent Application No. 32 134, published Jul. 15, 1981.

The cloning and expression of mature rIFN-α is described by Goeddel et al., *Nucleic Acids Res.* 8, 4057 (1980).

The cloning and expression of mature rIFN-γ are described by Gray et al., *Nature* 295, 503 (1982).

All of the known IFNs-α, -β, and -γ contain multiple cysteine residues. These residues contain sulfhydryl side-chains which are capable of forming intermolecular disulfide bonds. For example, the amino acid sequence of mature recombinant rIFN-αA contains cysteine residues at positions 1, 29, 98 and 138. Wetzel et al., *Nature* 289, 606 (1981), assigned intramoleculardisulfide bonds between the cysteine residues at positions 1 and 98, and between the cysteine residues at positions 29 and 138.

Antibodies specifically binding various interferons are also well known in the art. For example, anti-α-interferon agonist antibodies have been reported by Tsukui et al., *Microbiol. Immunol.* 30, 1129–1139 (1986); Duarte et al., *Interferon-Biotechnol.* 4, 221–232 (1987); Barasoain et al., J. Immunol. 143, 507–512 (1989) Exley et al., *J. Gen. Virol.* 65, 2277–2280 (1984); Shearer et al., *J. Immunol.* 133, 3096–3101 (1984); Alkan et al., *Ciba Geigy Foundation Symposium* 119, 264–278 (1986); Noll et al., *Biomed. Biochim. Acta* 48, 165–176 (1989); Hertzog et al., *J. Interferon Res.* 10(Suppl. 1) (1990); Kontsek et al., *J. Interferon Res. (special issue)* 327–322 (1991), and U.S. Pat. No. 4,423,147 issued Dec. 27, 1983.

Interferons have a variety of biological activities, including antiviral, immunoregulatory and antiproliferative properties, and are, therefore, of great interest as therapeutic agents in the control of cancer, and various viral diseases. Interferons have been implicated in the pathogenesis of various autoimmune diseases, such as systemic lupus erythematoses, Behcet's disease, insulin-dependent diabetes mellitus (IDDM, also referred to as type I diabetes). It has been demonstrated in a transgenic mouse model that β cell expression of IFN-α can cause insulitis and IDDM, and IFN-αantagonists (including antibodies) have been proposed for the treatment of IDDM (WO 93/04699, published Mar. 18,1993). Impaired IFN-γ and IFN-α production has been observed in multiple sclerosis (MP) patients. An acid-labile IFN-α has been detected in the serum of many AIDS patients, and it has been reported that the production of IFN-γ is greatly supressed in suspensions of mitogen-stimulated mononuclear cells derived from AIDS patients. For a review see, for example, Chapter 16, "The Presence and Possible Pathogenic Role of Interferons in Disease", In: *Interferons and other Regulatory Cytokines*, Edward de Maeyer (1988, John Wilet and Sons publishers). Alpha and beta interferons have been used in the treatment of the acute viral disease herpes zoster (T. C. Merigan et al., *N. Engl. J. Med.* 298, 981–987 (1978); E. Heidemann et al., *Onkologie* 210–212 (1984)), chronic viral infections, e.g. hepatitis B infections (R. L. Knobler et al., *Neurology* 34, 1273–279 (1984); M. A. Farkkila et al., *Act. Neurol. Sci.* 87, 325–328 (1993)). rIFNα-2a (Roferon®, Roche) is an injection formulation indicated in use for the treatment of hairy cell leukemia and AIDS-related Kaposi's sarcoma. Recombinant IFN-α-2b (Intron® A, Schering) has been approved for the treatment of hairy cell leukemia, selected cases of condylomata acuminata, AIDS-related Kaposis's sarcoma, chronic hepatitis Non-A, Non-B/C, and chronic helatitis B infections is certain patients. IFN-γ-1 b (Actimmune®, Genentech, Inc.) is commercially available for the treatment of chronic granumatous disease.

SUMMARY OF THE INVENTION

Applicants have identified a cDNA clone (designated in the present application as "DNA50960") that encodes a novel human interferon polypeptide.

In one embodiment, the invention provides an isolated nucleic acid molecule comprising DNA having at least a 95% sequence identity to (a) a DNA molecule encoding a novel human interferon polypeptide designated PRO655 comprising the sequence of amino acids from about 22 to 189 of FIG. 1 (SEQ ID NO: 1), or (b) the complement of the DNA molecule of (a). In one aspect, the isolated nucleic acid comprises DNA encoding a new interferon polypeptide polypeptide having at least amino acid residues 22 to 189 of FIG. 1 (SEQ ID NO:1), or is complementary to such encoding nucleic acid sequence, and remains stably bound to it under at least moderate, and optionally, under high stringency conditions. In another embodiment, the isolated nucleic acid molecule encodes the full-length polypeptide represented in FIG. 1 (SEQ. ID. NO: 1), with or without the putative signal peptide at amino acids 1–21, and with or without the initiating methionine, or is the complement of such DNA molecule. In a further embodiment, the isolated nucleic acid molecule comprises DNA having at least a 95% sequence identity to (a) DNA molecule encoding the same mature polypeptide encoded by the human interferon protein cDNA in ATCC Deposit No.209509 (DNA50960–1224).

In another embodiment, the invention provides a vector comprising DNA (as hereinabove defined) encoding a novel interferon polypeptide. A host cell comprising such a vector is also provided. By way of example, the host cells may be CHO cells, *E. coli*, or yeast (including *Saccharomyces cerevisiae* and other yeast strains). A process for producing the new interferon polypeptides of the present invention is further provided and comprises culturing host cells under conditions suitable for expression of the desired interferon polypeptide, and recovering the interferon from the cell culture.

In another embodiment, the invention provides novel, isolated interferon polypeptides. In particular, the invention provides isolated a native interferon polypeptide, which in one embodiment, includes an amino acid sequence comprising residues 22 to 189 of FIG. 1 (SEQ ID NO:1).

In another embodiment, the invention provides chimeric molecules comprising a novel interferon polypeptide herein fused to a heterologous polypeptide or amino acid sequence. An example of such a chimeric molecule comprises an interferon polypeptide fused to an epitope tag sequence or an immunoglobulin heavy or light chain constant region sequence, e.g. the Fc region of an immunoglobulin.

In another embodiment the invention provides an antibody which specifically binds to a novel interferon polypeptide disclosed herein Optionally, the antibody is a monoclonal antibody.

BRIEF DESCRIPTION OF THE DRAWINGS

FIG. 1 shows the derived amino acid sequence of a native sequence human interferon polypeptide designated PRO655 (SEQ ID NO: 1). Amino acids 1 to 21 have been identified as a putative signal sequence, using the method of G. von Heijne, *N.A.R.* 14 4683 (1986).

FIG. 2 shows the nucleotide sequence of a native sequence PRO655 interferon cDNA (SEQ ID NO: 2). The ATG start codon encoding the N-terminal initiating methionine residue is indicated.

FIGS. 3A–B show the nucleotide sequence (SEQ ID NO:2), complimentary sequence (SEQ ID NO:3), and the derived amino acid sequence[s] (SEQ ID NO:1) of the native sequence human interferon polypeptide PRO655.

FIGS. 4A–B are the alignments of the amino acid sequence encoded by DNA50960 with known amino acid sequences of human IFNsβ (SEQ ID NO:7), α1 (SEQ ID NO:8), α2 (SEQ ID NO:9), α4 (SEQ ID NO:10), α5 (SEQ ID NO:11), α6 (SEQ ID NO:12), α7 (SEQ ID NO:13), α8 (SEQ ID NO:14), αA (SEQ ID NO:15), αD (SEQ ID NO:16), αF (SEQ ID NO:17), αG (SEQ ID NO: 18), and αK (SEQ ID NO:19). The alignment shows the conservation of thecysteines at positions 53 and 163 in the protein endcoded by DNA50960, and indicates a unique cysteine at positon 175. There is a potential disulfide bond between positons 53-163 or 53-175.

FIG. 6 shows the nucleotide sequence (SEQ ID NO:20), complimentary sequence (SEQ ID NO:21) and the deduced amino acid sequence[s] (SEQ ID NO:22) of DNA 49668 used in the cloning of DNA50960.

DETAILED DESCRIPTION OF THE PREFERRED EMBODIMENTS

II. Definitions

Figure 5:
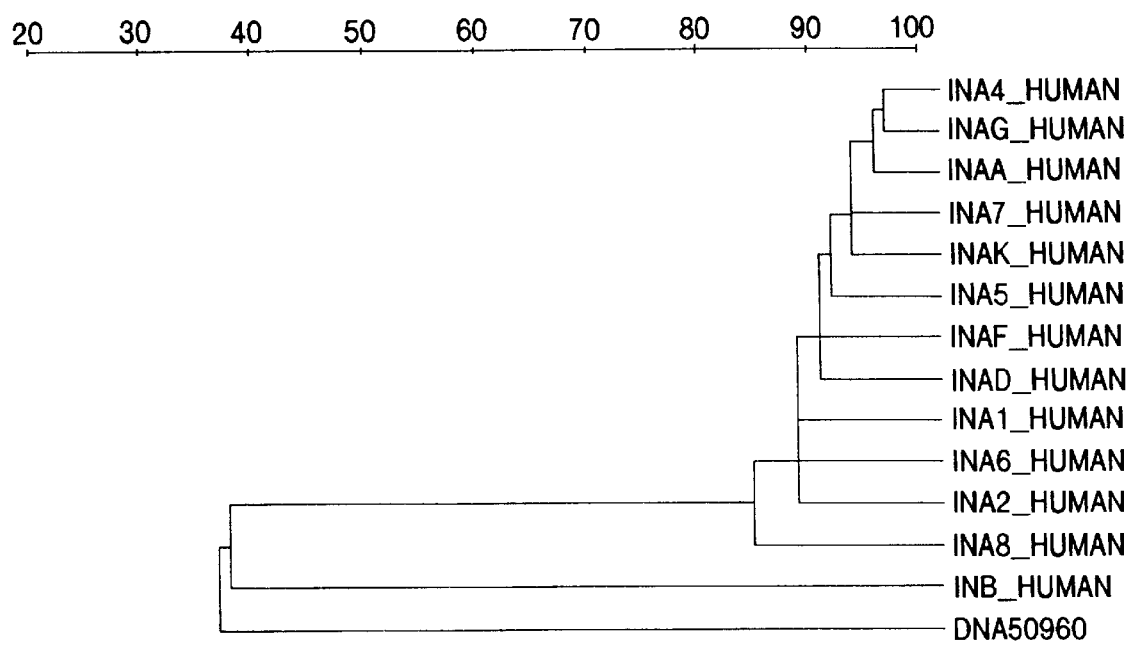
FIG. 5 is a diagram illustrating the relationship of various human α interferon and human β interferon with the novel interferon encoded by DNA50960.

The terms "interferon (IFN) polypeptide", "PRO655 polypeptide" and "PRO655" when used herein encompass native sequence PRO655 and PRO655 variants (which are further defined herein). The novel IFN polypeptide, designated PRO655, may be isolated from a variety of sources, such as from human tissue types or from another source, or prepared by recombinant or synthetic methods, or by any combination of these or similar techniques.

A "native sequence interferon (IFN) polypeptide" or "native sequence PRO655 polypeptide" or "native sequence PRO655", which terms ar used interchangeably, comprises a polypeptide having the same amino acid sequence as a PRO655 polypeptide derived from nature. Such native sequence PRO655 can be isolated from nature or can be produced by recombinant or synthetic means. The term "native sequence PRO655" specifically encompasses naturally-occurring truncated forms of the PRO655 polypeptide, naturally-occurring variant forms (e.g., alternatively spliced forms) and naturally-occurring allelic variants of the native sequence interferon polypeptide herein. In one embodiment of the invention, the native sequence PRO655 is a mature or full-length native sequence PRO655 comprising amino acids 22 to 208 of FIG. I (SEQ ID NO:1).

"PRO655 variant" means an active PRO655 as defined below encoded by a nucleic acid comprising DNA having at least about 80% nucleic acid sequence identity to (a) a DNA molecule encoding a PRO655 polypeptide, with or without its signal sequence, or (b) the complement of the DNA molecule of (a). In a particular embodiment, the "PRO655 variant" has at least about 80% amino acid sequence identity with the PRO655 having the deduced amino acid sequence shown in FIG. 1 (SEQ ID NO:1) for a full-length native sequence PRO655. Such PRO655 variants include, for instance, PRO655 polypeptides wherein one or more amino acid residues are added, or deleted at te N- or C-terminus of the sequence of FIG. 1 (SEQ ID NO:1). Preferably, the nucleic acid or amino acid sequence identity is at least about 85%, more preferably at least about 90%, and even more preferably at least about 95%.

"Percent (%) amino acid sequence identity" with respect to the PRO655 sequences identified herein is defined as the percentage of amino acid residues in a candidate sequence that are identical with the amino acid residues in the PRO655sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the PRO655 sequences identified herein is defined as the percentage of nucleotides in a candidate sequence that are identical with the nucleotides in the PRO655 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR)software. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO655 natural environment will not be present. Ordinarily, however, isolated polypeptide will be prepared by at least one purification step.

An "isolated" nucleic acid molecule encoding PRO655 is a nucleic acid molecule that is identified and separated from at least one contaminant nucleic acid molecule with which it is ordinarily associated in the natural source of the PRO655-encoding nucleic acid. An isolated nucleic acid molecule is other than in the form or setting in which it is found in nature. Isolated nucleic acid molecules encoding PRO655 therefore are distinguished from the PRO655-encoding nucleic acid molecule as it exists in natural cells. However, an isolated nucleic acid molecule encoding PROO0655 includes nucleic acid molecules contained in cells that ordinarily express PRO655 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-PRO655 monoclonal antibodies (including agonist, antagonist, and neutralizing antibodies) and anti-PRO655 antibody compositions with polyepitopic specificity. The term "monoclonal antibody" as used herein refers to an antibody obtained from a population of substantially homogeneous antibodies, i.e., the individual antibodies comprising the population are identical except for possible naturally occurring mutations that may be present in minor amounts. "Active" or "activity" for the purposes herein refers to form(s) of PRO655 which retain the biologic and/or immunologic activities of native or naturally-occurring PRO655. Preferred biological activities include, but are not limited to, antiviral, immunoregulatory or antiproliferative properties.

II. Compositions and Methods of the Invention

A. Full-Length PRO655 Human Interferon Polypeptide

The present invention provides newly identified and isolated nucleotide sequences encoding novel human interferon polypeptides referred to in the present application as PRO655. In particular, Applicants have identified and isolated cDNA encoding a PRO655 polypeptide, as disclosed in further detail in the Examples below. Using BLAST and FastA sequence alignment computer programs, Applicants found that a full-length native sequence PRO655 (shown in FIG. 1 and SEQ ID NO:1) has about 35–40% amino acid sequence identity with the sequence of various human IFN-α species. The homology is highest within the 22–189 amino acid region of the sequence of FIG. 1 (SEQ ID NO: 1). At the nucleotide level, the homology with the coding sequence of IFN-α is about 60%. Accordingly, it is presently believed that PRO655 disclosed in the present application is a newly identified, novel member of the human interferon family and may possess antiviral, immunoregulatory and/or antiproliferative activities typical of the human interferon family. The relationship of this distinct, novel human interferon to some known IFNα species and IFN-β is illustrated in FIG. 5.

B. PRO655 Variants

In addition to the full-length native sequence PRO655 described herein, it is contemplated that PRO655 variants can be prepared. PRO655 variants can be prepared by introducing appropriate nucleotide changes into the DNA encoding PRO655, or by synthesis of the desired PRO655 polypeptide. Those skilled in the art will appreciate that amino acid changes may alter post-translational processes of the PRO655, such as changing the number or position of glycosylation sites or altering the membrane anchoring characteristics.

It is well known that interferons tend to oligomerize. Although the etiology of these oligomers is not entire understood, it is believed, that certain oligomeric forms result from two or more interferon molecules becoming irreversibly associated with one another through intermolecular covalent bonding, such as by disulfide linkages. This problems has been observed particularly with respect to leukocyte and fibroblast interferons. (See, e.g. U.S. Pat. No. 4,816,566.) Accordingly, it may be desirable to prepare amino acid variants of the native PRO655 polypeptides of the present invention in which one or more cysteine residues are deleted or substituted by residues of other amino acids which are incapable of disulfide bond formation. Preferred variants substantially retain the biological activity of the PRO655 from which they are derived. As noted before, the native PRO655 sequence includes cysteine residues at positions 53, 163 and 175 in the sequence of FIG. 1 (SEQ ID NO:1). In a preferred embodiment, at least one of the cysteine residues at positions 53, 163, and 175 is replaced by amino acid residues that are incapable of forming intermolecular disulfide bonds.

Variations in the native full-length sequence PRO655 or in various domains of the PRO655 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO655 that results in a change in the amino acid sequence of the PRO655 as compared with the native sequence PRO655. Optionally the variation is by substitution of at least one amino acid with any other amino acid in one or more of the domains of the PRO655. Guidance in determining which amino acid residue may be inserted, substituted or deleted without adversely affecting the desired activity may be found by comparing the sequence of the PRO655 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variation scan be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene,* 34:315 (1985)], restriction selection mutagenesis [Wells et al., *Phi-los. Trans. R. Soc. London SerA,* 317:415 (1986)] or other known techniques can be performed on the cloned DNA to produce the PRO655 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO655

Covalent modifications of PRO655 are included within the scope of this invention. One type of covalent modification includes reacting targeted amino acid residues of the PRO655 with an organic derivatizing agent that is capable of reacting with selected side chains or the N- or C-terminal residues of the PRO655. Derivatization with bifunctional agents is useful, for instance, for crosslinking PRO655 to a water-insoluble support matrix or surface for use in the method for purifying anti-PRO655 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRO655 polypeptide included within the scope of this invention comprises altering the native glycosylation pattern of the polypeptide. "Altering the native glycosylation pattern" is intended for purposes herein to mean deleting one or more carbohydrate moieties found in native sequence PRO655, and/or adding one or more glycosylation sites that are not present in the native sequence PRO655.

Addition of glycosylation sites to the PRO655 polypeptide may be accomplished by altering the amino acid sequence. The alteration may be made, for example, by the addition of, or substitution by, one or more serine or threonine residues to the native sequence PRO655 (for O-linked glycosylation sites). The PRO655 amino acid sequence may optionally be altered through changes at the DNA level, particularly by mutating the DNA encoding the PRO655 polypeptide at preselected bases such that codons are generated that will translate into the desired amino acids.

Another means of increasing the number of carbohydrate moieties on the PRO655 polypeptide is by chemical or enzymatic coupling of glycosides to the polypeptide. Such methods are described in the art, e.g., in WO 87/05330 published Sept. 11, 1987, and in Aplin and Wriston, *CRC Crit. Rev. Biochem.*, pp. 259–306 (1981).

Removal of carbohydrate moieties presention the PRO655 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO655 comprises linking the PRO655 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The PRO655 of the present invention may also be modified in a way to form a chimeric molecule comprising PRO655 fused to another, heterologous polypeptide or amino acid sequence. In one embodiment, such a chimeric molecule comprises a fusion of the PRO655 with a tag polypeptide which provides an epitope to which an anti-tag antibody can selectively bind. The epitope tag is generally placed at the amino- or carboxyl-terminus of the PRO655. The presence of such epitope-tagged forms of the PRO655 can be detected using an antibody against the tag polypeptide. Also, provision of the epitope tag enables the PRO655 to be readily purified by affinity purification using an anti-tag antibody or another type of affinity matrix that binds to the epitope tag. In an alternative embodiment, the chimeric molecule may comprise a fusion of the PRO655 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine(poly-his-gly) tags; the flu HA tag polypeptide and its antibody 12CA5 [Field et al., *Mol. Cell. Biol.*, 8:2159–2165(1988)]; the c-myc tag and the 8F9, 3C 7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 [Lutz-Freyermuth et al., *Proc. Natl. Acad. Sci. USA*, 87:6393–6397 (1990)].

D. Preparation of PRO655

The description below relates primarily to production of PRO655 by culturing cells transformed or transfected with a vector containing nucleic acid encoding PRO655. It is, of course, contemplated that alternative methods, which are well known in the art, may be employed to prepare PRO655. For instance, the PRO655 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturers's instructions. Various portions of the PRO655 may be chemically synthesized separately and combined using chemical or enzymatic methods to produce the full-length PRO655.

1. Isolation of DNA Encoding PRO655

DNA encoding PRO655 may be obtained from a cDNA library prepared from tissue believed to possess the PRO655 mRNA and to express it at a detectable level. Accordingly, human PRO655 DNA can be conveniently obtained from a cDNA library prepared from human tissue, such as described in the Examples. The PRO655-encoding gene may also be obtained from a genomic library or by oligonucleotide synthesis.

Libraries can be screened with probes (such as antibodies to the PRO655 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO655 is to use PCR methodology [Sambrook et al., supra; Dieffenbach et al., *PCR Primer A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Gen-Bank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO655 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Virology,* 2:456–457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceaesuch as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentousfungi or yeast are suitable cloning or expression hosts for PRO655-encoding vectors. Saccharomyces cerevisiae is a commonly used lower eukaryotic host microorganism.

Suitable host cells for the expression of glycosylated PRO655 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 3:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO655 may be inserted into a replicable vector for cloning (amplification of the DNA) or for expression. Various vectors are publicly available. The vector may, for example, be in the form of a plasmid, cosmid, viral particle, or phage. The appropriate nucleicacid sequence may be inserted in to the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO655 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO655-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, rnethotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO655 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4–1 [Jones, *Genetics,* 85:12 (1977)].

Expression and cloning vectors usually contain a promoter operably linked to the nucleic acid sequence encoding PRO655 to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding PRO655.

Examples of suitable promoting sequences for use with yeast hosts include the promoters for 3-phosphoglyceratekinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose6-phosphateisomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO655 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO655 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO655 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO655.

Still other methods, vectors, and host cells suitable for adaptation to the synthesis of PRO655 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyconal, and may be prepared in any mammal. Conveniently, the antibodies may be prepared against a native sequence PRO655 polypeptideor against a synthetic peptide based on the DNA sequences provided herein or against exogenous sequence fused to PRO655 DNA and encoding a specific antibody epitope.

5. Purification of Polypeptide

Forms of PRO655 may be recovered from culture medium or from host cell lysates. If membrane-bound, it can be released from the membrane using a suitable detergent solution (e.g. Triton-X 100) or by enzymatic cleavage. Cells employed in expression of PRO655 can be disrupted by various physical or chemical means, such as freeze-thaw cycling, sonication, mechanical disruption, or cell lysing agents.

It may be desired to purify PRO655 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-taggedforms of the PRO655. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO655 produced.

E. Uses for PRO655

Nucleotide sequences (or their complement) encoding PRO655 have various applications in the art of molecular biology, including uses as hybridization probes, in chromosome and gene mapping and in the generation of anti-sense RNA and DNA. PRO655 nucleic acid will also be useful for the preparation of PRO655 polypeptides by the recombinant techniques described herein.

The full-length native sequence gene encoding PRO655 (DNA50960, FIG. 2, SEQ ID NO: 2), or portions thereof, may be used as hybridization probes for a cDNA library to isolate the full-length gene or to isolate still other genes (for instance, those encoding naturally-occurring variants of PRO655 or PRO655 from other species) which have a desired sequence identity to the PRO655 sequence disclosed in FIG. 2 (SEQ ID NO:2). Optionally, the length of the probes will be about 20 to about 50 bases. The hybridization probes may be derived from the nucleotide sequence of SEQ ID NO: 2 or from genomic sequences including promoters, enhancer elements and introns of native sequence PRO655. By way of example, a screening method will comprise isolating the coding region of the PRO655 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidinibiotin coupling systems. Labeled probes having a sequence complementary to that of the PRO655 gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related PRO655 sequences.

Nucleotide sequences encoding a PRO655 polypeptide can also be used to construct hybridization probes for mapping the gene which encodes that PRO655 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. Other interferons, e.g. IFNs-α1, α8, α10, α14, α16, α21, β1, and omega1 have been mapped to Chromosome 9.

The novel PRO655 human interferon can also be used in assays to identify and purify its receptor, and to identify other proteins or molecules involved in the ligand/receptor binding interaction. By such methods, inhibitors of the receptor Aigand binding interaction can be identified. Proteins involved in such binding interactions can also be used to screen for peptide or small molecule inhibitors or agonists of the binding interaction. Screening assays can be designed to find lead compounds that mimic the biological activity of a native PRO655 interferon or a receptor for PRO655. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO655 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO655 can be used to clone genomic DNA encoding PRO655 in accordance with established techniques and the genomic sequences used to generate transgenic animals that contain cells which express DNA encoding PRO655. Methods for generating transgenic animals, particularly animals such as mice or rats, have become conventional in the art and are described, for example, in U.S. Pat. Nos. 4,736,866 and 4,870,009. Typically, particular cells would be targeted for PRO655 transgene incorporation with tissue-specific enhancers. Transgenic animals that include a copy of a transgene encoding PRO655 introduced into the germ line of the animal at an embryonic stage can be used to examine the effect of increased expression of DNA encoding PRO655. Such animals can be used as tester animals for reagents thought to confer protection from, for example, pathological conditions associated with its over expression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO655can be used to constructa PRO655 "knock out" animal which has a defective or altered gene encoding PRO655 as a result of homologous recombination between the endogenous gene encoding PRO655 and altered genomic DNA encoding PRO655 introduced into an embryonic cell of the animal. For example, cDNA encoding PRO655 can be used to clone genomic DNA encoding PRO655 in accordance with established techniques. A portion of the genomic DNA encoding PRO655 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51503 (1987) for a description of homologous recombination vectors]. The vector is introduced into an embryonic stem cell line (e.g., by electroporation)and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp.113–152]. A chimeric embryo can then be implanted into a suitable pseudopregnant female foster animal and the embryo brought to term to create a "knock our" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO655 polypeptide.

The novel PRO655 human interferon polypeptides of the present invention are expected to have antiviral, antiproliferative and/or immunoregulatory activities. Thus, PRO655, including its variants and derivatives, might be used for the treatment of malignant or non-malignant conditions associated with unwanted cell proliferation, or viral diseases. More particularly, PRO655 may be useful for the treatment of diseases characterized by tumorigenic or neoplastic cell growth, malignant hematological systemic diseases, viral disease, asthma, carcinopmas,sarcomas, myelomas, melanomas, lymphomas, papillomas, degenerative diseases, allergic diseases psoriasis and pain. Dosages can be calculated based upon the specific activity of PRO655 as compared to the specific activities of other, known interferons, which have been used to treat similar conditions.

F. Anti-PRO655 Antibodies

The present invention further provides anti-PRO655antibodies. Exemplary antibodies include polyclonal, monoclonal, humanized, bispecific, and heteroconjugate antibodies.

1. Polyclonal Antibodies

The anti-PRO655 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO655 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freunds's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO655 antibodies may, alternatively, be monoclonal antibodies. Monoclonal antibodies may be prepared using hybridoma methods, such as those described by Kohler and Milstein, *Nature*, 2:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the anti-PRO655 polypeptide or a fusion protein thereof. Generally, either peripheral blood lymphocytes("PBLs")are used if cells of human origin are desired, or spleen cells or lymph node cells are used if non-human mammalian sources are desired. The lymphocytes are then fused with an immortalized cell line using a suitable fusing agent, such as polyethyleneglycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against anti-PRO655. Preferably, the binding specificity of monoclonal antibodies produced by the hybridoma cells is determined by immunoprecipitationor by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbeccos's Modified Eagles's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra) orby covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-PRO655 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or frame work sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the PRO655, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/ light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93108829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-PRO655 Antibodies

The anti-PRO655 antibodies of the invention have various utilities. For example, anti-PRO655 antibodies may be used in diagnostic assays for PRO655, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Ani-PRO655 antibodies also are useful for the affinity purification of PRO655 from recombinant cell culture or natural sources. In this process, the antibodies against PRO655 are immobilized on a suitable support, such a Sephadex resin or filter paper, using methods well known in the art. The immobilized antibody then is contacted with a sample containing the PRO655 to be purified, and thereafter the support is washed with a suitable solvent that will remove substantially all the material in the sample except the PRO655, which is bound to the immobilized antibody. Finally, the support is washed with another suitable solvent that will release the PRO655 from the antibody.

As noted before, interferons have been implicated in the pathogenesis of various autoimmune diseases, such as systemic *lupus erythematoses*, Behcets's disease, insulin-dependent *diabetes mellitus* (IDDM, also referred to as type I diabetes), and antibodies to various interferons the overexpression of which has been associated with the development and pathogenesis of such diseases have been proposed as potential therapeutics. For example, it has been demonstrated in a transgenic mouse model that β cell expression of IFNα can cause insulitis and IDDM, and IFNα antagonists (including antibodies) have been proposed for the treatment of IDDM (WO 93/04699, published Mar. 18, 1993). Accordingly, anti-PRO655 antibodies might be useful in the treatment of diseases associated with the overexpression of PRO655.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturers's instructions unless otherwise indicated. The source of those cells identified in the following examples, and throughout the specification, by ATCC accession numbers is the American Type Culture Collection, Rockville, Md.

Example 1

Isolation of cDNA Clones Encoding Human PRO655

An expressed sequence tag (EST) DNA database (LIFESEQ™, Incyte Pharmaceuticals, Palo Alto, Calif.) was searched and an EST was identified which showed homology to interferon-α. Possible homology was noted between Incyte EST 3728969 (subsequently renamed as DNA49668) and mammalian alpha interferons. The homology was confirmed by inspection.

The following PCR primers and oligonucleotide probe were synthesized:

49668.r1:

```
49668.r1:
TCTCTGCTTCCAGTCCCATGAGTGC                                    (SEQ ID NO:4)

49668.r2:
GCTTCCAGTCCCATGAGTGCTTCTAGG                                  (SEQ ID NO:5)

49668.p1:
GGCCATTCTCCATGAGATGCTTCAGCAGATCTTCAGCCTCTTCAGGGCAA           (SEQ ID NO:6)
```

In order to screen several libraries for a source of a full-length clone, DNA from the libraries was screened using the r1 and r2 probes identified above. A positive library was then used to isolate clones encoding the PRO655-encoding gene using the probe oligonucleotide.

Three million clones from a size selected (500–4000 bp) oligo dT primed cDNA library from human small intestine (LIB 99) constructed in a pRK5-based vector screened by hybridization. The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI sites.

DNA sequencing of the clones isolated as described above gave the full-length DNA sequence for DNA50960 and the derived protein sequence for PRO655.

The entire nucleotide sequence of DNA50960 is shown in FIG. 2 (SEQ ID NO:2). Clone DNA50960 contains a single open reading frame with an apparent translational initiation site at nucleotide positions 621–623 (FIG. 2). The predicted polypeptide precursor is 208 amino acids long, of which 21 N-terminal amino acid residues represent a putative signal sequence. Clone DNA50960-1224 has been deposited with ATCC and is assigned ATCC deposit no. 209509.

Using BLAST and FastA sequence alignment computer programs, it was found that PRO655 (shown in FIG. 1 and SEQ ID NO:1) has about 35–40% amino acid sequence identity with the sequence of various human IFN-α species. The homology is highest within the 22–189 amino acid region of the sequence of FIG. 1 (SEQ ID NO: 1). At the nucleotide level, the homology with the coding sequence of IFN-α is about 60%.

Example 2

Use of the Novel Human Interferon Encoding PRO655 as a Hybridization Probe

The following method describes use of a nucleotide sequence encoding PRO655 as a hybridization probe.

DNA comprising the coding sequence of PRO655 (as shown in FIG. 2, SEQ ID NO:2) is employed as a probe to screen for homologous DNAs (such as those encoding naturally-occurring variants of PRO655) in human tissue cDNA libraries or human tissue genomic libraries.

Hybridization and washing of filters containing either library DNAs is performed under the following high stringency conditions. Hybridization of radiolabeled probe derived from the PRO655-encoding DNA, to the filters is performed in a solution of 50% formamide, 5×SSC, 0.1% SDS, 0.1% sodium pyrophosphate, 50 mM sodium phosphate, pH 6.8, 2×Denhardts's solution, and 10% dextran sulfate at 42° C. for 20 hours. Washing of the filters is performed in an aqueous solution of 0.1 ×SSC and 0.1% SDS at 42° C.

DNAs having a desired sequence identity with the DNA encoding full-length native sequence PRO655 can then be identified using standard techniques known in the art.

Example 3

Expression of PRO655 in *E. coli*

This example illustrates preparation of an unglycosylated form of PRO655 by recombinant expression in *E. coli*.

The DNA sequence encoding PRO655 (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*, see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO655 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO655 protein can then be purified using a metal chelating column under conditions that allow tight binding of the protein.

Example 4

Expression of PRO655 in Mammalian Cells

This example illustrates preparation of a glycosylated form of PRO655 by recombinant expression in mammalian cells.

The vector, pRK5 (see EP 307,247, published Mar. 15, 1989), is employed as the expression vector. Optionally, the PRO655-encoding DNA is ligated into pRK5 with selected restriction enzymes to allow insertion of the PRO655-encoding DNA using ligation methods such as described in Sambrook et al., supra. The resulting vector is called pRK5-PRO655.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO655 DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µg of 50 mM HEPES (pH 7.35),280 mM NaCl. 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections,the culture medium is removed and replaced with culture medium (alone) or culture medium containing 200 µCi/ml $^{35}$S-cysteine and 200 µCi/ml$^{35}$ S-methionine. After a 12 hour incubation, the conditioned medium is collected, concentrated on a spin filter, and loaded onto a 15% SDS gel. The processed gel may be dried and exposed to film for a selected period of time to reveal the presence of PRO655 polypeptide. The cultures containing transfected cells may undergo further incubation (in serum free medium) and the medium is tested in selected bioassays.

In an alternative technique, DNA encoding PRO655 may be introduced into 293 cells transiently using the dextran sulfate method described by Sompayrnc et al., *Proc. Natl. Acad. Sci.*, 78:7575 (1981). 293 cells are grown to maximal density in a spinner flask and 700 µg pRK5-PRO655 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO655 can then be concentrated and purified by any selected method, such as dialysis andlor column chromatography.

In another embodiment the novel interferon polypeptide (PRO655) can be expressed in CHO cells. The pRK5-PRO655 DNA can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO655 polypeptide, the culture medium may be replaced with serum free medium. Preferably, the cultures are incubated for about 6 days, and then the conditioned medium is harvested. The medium containing the expressed PRO655 then be concentrated and purified by any selected method.

Epitope-tagged PRO655 DNA may also be expressed in host CHO cells. The PRO655 DNA may be subcloned out of the pRK5 vector. The subclone insert can undergo PCR to fuse in frame with a selected epitope tag such as a poly-his tag into a Baculovirus expression vector. The poly-his tagged insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO655 can then be concentrated and purified by any selected method, such as by $Ni^{2+}$-chelate affinity chromatography.

Example 5

Expression of PRO655 in Yeast

The following method describes recombinant expression of PRO655 in yeast.

First, yeast expression vectors are constructed for intracellular production or secretion of PRO655 from the ADH2/GAPDH promoter. DNA encoding PRO655, a selected signal peptide and the promoter is inserted into suitable restriction enzyme sites in the selected plasmid to direct intracellular expression of PRO655. For secretion, DNA encoding PRO655 can be cloned into the selected plasmid, together with DNA encoding the ADH2/GAPDH promoter, the yeast alpha-factor secretory signal/leader sequence, and linker sequences (if needed) for expression of POR0655.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO655 can subsequently be isolated and purified by removing the yeast cells from the fermentation medium by centrifugation and then concentrating the medium using selected cartridge filters. The concentrate containing PRO655 may further be purified using selected column chromatography resins.

Example 6

Expression of PRO655 in Baculovirus-infected Insect Cells

The following method describes recombinant expression of PRO655 in Baculovirus expression system.

The PRO655-encoding DNA is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the coding sequence of PRO655 or the desired portion of the coding sequence is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released is viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PRO655 can then be purified, for example, by $Ni^{2+}$-chelate affinity chromatography as follows. Extracts are prepared from recombinant virus-infected Sf9 cells as described by Ruppert et al., *Nature*, 362:175–179(1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkalinephosphatase(Qiagen). Fractions containing the eluted $His_{10}$-tagged PRO655 are pooled and dialyzed against loading buffer.

Alternatively, purification of the IgG tagged (or Fc tagged) PRO655 can be performed using known chromatography techniques, including for instance, Protein A or protein G column chromatography.

Example 7

Preparation of Antibodies that Bind PRO655

This example illustrates preparation of monoclonal antibodies which can specifically bind PRO655.

Techniques for producing the monoclonal antibodies are known in the art and are described, for instance, in Goding, supra. Immunogens that may be employed include purified PRO655, fusion proteins containing PRO655, and cells expressing recombinant PRO655 on the cell surface. Selection of the immunogen can be made by the skilled artisan without undue experimentation.

Mice, such as Balb/c, are immunized with the PRO655 immunogen emulsified in complete Freunds's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animals's hind foot pads. The immunized mice are then boosted 10 to 12 days later with additional immunogen emulsified in the selected adjuvant Thereafter, for several weeks, the mice may also be boosted with additional immunization injections. Serum samples may be periodically obtained from the mice by retro-orbital bleeding for testing in ELISA assays to detect anti-PRO655 antibodies.

After a suitable antibody titer has been detected, the animals "positive" for antibodies can be injected with a final intravenous injection of PRO655. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO655. Determination of "positive" hybridoma cells secreting the desired monoclonal antibodies against PRO655 is within the skill in the art.

The positive hybridoma cells can be injected intraperitoneally into syngeneic Balb/c mice to produce ascites containing the anti-PRO655 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively,affinity chromatography based upon binding of anbbodyto proteinA or protein G can be employed.

Deposit of Material

The following material has been deposited with the American Type Culture Collection, 12301 Parklawn Drive, Rockville, Md., USA (ATCC):

| Material | ATCC Dep. No. | Deposit Date |
| --- | --- | --- |
| DNA50960-1224 | 209509 | December 3, 1997 |

This deposit was made under the provisions of the Budapest Treaty on the International Recognition of the Deposit of Microorganisms for the Purpose of Patent Procedure and the Regulations thereunder(BudapestTreaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioners's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

SEQUENCE LISTING

<160> NUMBER OF SEQ ID NOS: 22

<210> SEQ ID NO 1
<211> LENGTH: 200
<212> TYPE: PRT
<213> ORGANISM: Homo sapiens

<400> SEQUENCE: 1

```
Met Ile Ile Lys His Phe Phe Gly Thr Val Leu Val Leu Leu Ala
 1               5                  10                  15

Ser Thr Thr Ile Phe Ser Leu Asp Leu Lys Leu Ile Ile Phe Gln
                20                  25                  30

Gln Arg Gln Val Asn Gln Glu Ser Leu Lys Leu Leu Asn Lys Leu
                35                  40                  45

Gln Thr Leu Ser Ile Gln Gln Cys Leu Pro His Arg Lys Asn Phe
                50                  55                  60

Leu Leu Pro Gln Lys Ser Leu Ser Pro Gln Gln Thr Gln Lys Gly
                65                  70                  75

His Thr Leu Ala Ile Leu His Glu Met Leu Gln Gln Ile Phe Ser
                80                  85                  90

Leu Phe Arg Ala Ile Ser Leu Asp Gly Trp Glu Glu Asn His Thr
                95                 100                 105
```

```
Glu Lys Phe Leu Gln Leu His Gln Gln Leu Glu Tyr Leu Glu Ala
                110                 115                 120
Leu Met Gly Leu Ala Glu Lys Leu Ser Gly Thr Leu Gly Ser Asp
            125                 130                 135
Asn Leu Arg Leu Val Lys Met Tyr Phe Arg Arg Ile His Asp Tyr
            140                 145                 150
Leu Glu Asn Gln Tyr Ser Thr Cys Ala Trp Ala Ile Val Gln Val
            155                 160                 165
Glu Ile Ser Arg Leu Phe Phe Val Phe Ser Leu Thr Glu Lys Leu
            170                 175                 180
Ser Lys Gln Gly Pro Leu Asn Asp Met Lys Gln Glu Leu Thr Thr
            185                 190                 195
Glu Phe Arg Ser Arg
            200

<210> SEQ ID NO 2
<211> LENGTH: 1502
<212> TYPE: DNA
<213> ORGANISM: Homo sapiens

<400> SEQUENCE: 2
cttagatatt aaactgatag gataagatat aaaataattt aagattgctg           50
atatatgttt taaaattaat tatttgctca agcatttgtg acaatttaca          100
gttctaattg aggttttaaa tttagtagtt tgtaggtatt ttaagttttg          150
cccctgaatt ctttataggt gctgataagc ctttggttaa gttttactcc          200
atgaaagact attactgaaa aaatgtaatc tcaataaaa  gaactttaat          250
aagcttgact aaatatttag aaagcacatt gtgttcagtg aaactttgta          300
tataatgaat agaataataa aagattatgt tggatgacta gtctgtaatt          350
gcctcaagga aagcatacaa tgaataagtt attttggtac ttcctcaaaa          400
tagccaacac aatagggaaa tggagaaaat gtactctgaa caccatgaaa          450
agggaacctg aaaatctaat gtgtaaactt ggagaaatga cattagaaaa          500
cgaaagcaac aaaagagaac actctccaaa ataatctgag atgcatgaaa          550
ggcaaacatt cactagagct ggaatttccc taagtctatg cagggataag          600
tagcatattt gaccttcacc atgattatca agcacttctt tggaactgtg          650
ttggtgctgc tggcctctac cactatcttc tctctagatt tgaaactgat          700
tatcttccag caaagacaag tgaatcaaga aagtttaaaa ctcttgaata          750
agttgcaaac cttgtcaatt cagcagtgtc taccacacag gaaaaacttt          800
ctgcttcctc agaagtcttt gagtcctcag cagtaccaaa aaggacacac          850
tctggccatt ctccatgaga tgcttcagca gatcttcagc ctcttcaggg          900
caaatatttc tctggatggt tgggaggaaa accacacgga gaaattcctc          950
attcaacttc atcaacagct agaataccta gaagcactca tgggactgga         1000
agcagagaag ctaagtggta ctttgggtag tgataacctt agattacaag         1050
ttaaaatgta cttccgaagg atccatgatt acctggaaaa ccaggactac         1100
agcacctgtg cctgggccat tgtccaagta gaaatcagcc gatgtctgtt         1150
ctttgtgttc agtctcacag aaaaactgag caaacaagga gacccttga          1200
acgacatgaa gcaagagctt actacagagt ttagaagccc gaggtaggtg         1250
```

| | |
|---|---|
| gagggactag aggacttctc cagacatgat tcttcataga gtggtaatac | 1300 |
| aatttatagt acaatcacat tgctttgatt ttgtgtatat atatatttat | 1350 |
| ctgagtttta agattgtgca tattgaccac aattgttttt attttgtaat | 1400 |
| gtggctttat atattctatc cattttaaat tgtttgtatg tcaaaataaa | 1450 |
| ttcattaata tggttgattc ttcaaaaaaa aaaaaaaaaa aaaaaaaaaa | 1500 |
| aa | 1502 |

<210> SEQ ID NO 3
<211> LENGTH: 1502
<212> TYPE: DNA
<213> ORGANISM: Homo sapiens

<400> SEQUENCE: 3

| | |
|---|---|
| tttttttttt tttttttttt tttttttttg aagaatcaac catattaatg | 50 |
| aatttatttt gacatacaaa caatttaaaa tggatagaat atataaagcc | 100 |
| acattacaaa ataaaacaa ttgtggtcaa tatgcacaat cttaaaactc | 150 |
| agataaatat atatatacac aaaatcaaag caatgtgatt gtactataaa | 200 |
| ttgtattacc actctatgaa gaatcatgtc tggagaagtc ctctagtccc | 250 |
| tccacctacc tcgggcttct aaactctgta gtaagctctt gcttcatgtc | 300 |
| gttcaagggt cttccttgtt tgctcagttt ttctgtgaga ctgaacacaa | 350 |
| agaacagaca tcggctgatt tctacttgga caatggccca ggcacaggtg | 400 |
| ctgtagtcct ggttttccag gtaatcatgg atccttcgga agtacatttt | 450 |
| aacttgtaat ctaaggttat cactacccaa agtaccactt agcttctctg | 500 |
| cttccagtcc catgagtgct tctaggtatt ctagctgttg atgaagttga | 550 |
| atgaggaatt tctccgtgtg gttttcctcc caaccatcca gagaaatatt | 600 |
| tgccctgaag aggctgaaga tctgctgaag catctcatgg agaatggcca | 650 |
| gagtgtgtcc ttttttggtac tgctgaggac tcaaagactt ctgaggaagc | 700 |
| agaaagtttt tcctgtgtgg tagacactgc tgaattgaca aggtttgcaa | 750 |
| cttattcaag agttttaaac tttcttgatt cacttgtctt tgctggaaga | 800 |
| taatcagttt caaatctaga gagaagatag tggtagaggc cagcagcacc | 850 |
| aacacagttc caaagaagtg cttgataatc atggtgaagg tcaaatatgc | 900 |
| tacttatccc tgcatagact tagggaaatt ccagctctag tgaatgtttg | 950 |
| cctttcatgc atctcagatt attttggaga gtgttctctt ttgttgcttt | 1000 |
| cgttttctaa tgtcatttct ccaagtttac acattagatt ttcaggttcc | 1050 |
| cttttcatgg tgttcagagt acattttctc catttcccta ttgtgttggc | 1100 |
| tattttgagg aagtaccaaa ataacttatt cattgtatgc tttccttgag | 1150 |
| gcaattacag actagtcatc caacataatc ttttattatt ctattcatta | 1200 |
| tatacaaagt ttcactgaac acaatgtgct ttctaaatat ttagtcaagc | 1250 |
| ttattaaagt tcttttattg agattacatt ttttcagta atagtctttc | 1300 |
| atggagtaaa acttaaccaa aggcttatca gcacctataa agaattcagg | 1350 |
| ggcaaaactt aaaataccta caaactacta aatttaaaac ctcaattaga | 1400 |
| actgtaaatt gtcacaaatg cttgagcaaa taattaattt taaaacatat | 1450 |

```
atcagcaatc ttaaattatt ttatatctta tcctatcagt ttaatatcta        1500
ag                                                              1502
```

<210> SEQ ID NO 4
<211> LENGTH: 25
<212> TYPE: DNA
<213> ORGANISM: Homo sapiens

<400> SEQUENCE: 4

```
tctctgcttc cagtcccatg agtgc                                       25
```

<210> SEQ ID NO 5
<211> LENGTH: 27
<212> TYPE: DNA
<213> ORGANISM: Homo sapiens

<400> SEQUENCE: 5

```
gcttccagtc ccatgagtgc ttctagg                                     27
```

<210> SEQ ID NO 6
<211> LENGTH: 50
<212> TYPE: DNA
<213> ORGANISM: Homo sapiens

<400> SEQUENCE: 6

```
ggccattctc catgagatgc ttcagcagat cttcagcctc ttcagggcaa            50
```

<210> SEQ ID NO 7
<211> LENGTH: 187
<212> TYPE: PRT
<213> ORGANISM: Homo sapiens

<400> SEQUENCE: 7

Met Thr Asn Lys Cys Leu Leu Gln Ile Ala Leu Leu Leu Cys Phe
  1               5                  10                  15

Ser Thr Thr Ala Leu Ser Met Ser Tyr Asn Leu Leu Gly Phe Leu
                 20                  25                  30

Gln Arg Ser Ser Asn Phe Gln Cys Gln Lys Leu Leu Trp Gln Leu
                 35                  40                  45

Asn Gly Arg Leu Glu Tyr Cys Leu Lys Asp Arg Met Asn Phe Asp
                 50                  55                  60

Ile Pro Glu Glu Ile Lys Gln Leu Gln Gln Phe Gln Lys Glu Asp
                 65                  70                  75

Ala Ala Leu Thr Ile Tyr Glu Met Leu Gln Asn Ile Phe Ala Ile
                 80                  85                  90

Phe Arg Gln Asp Ser Ser Ser Thr Gly Trp Asn Glu Thr Ile Val
                 95                 100                 105

Glu Asn Leu Leu Ala Asn Val Tyr His Gln Ile Asn His Leu Lys
                110                 115                 120

Thr Val Leu Glu Glu Lys Leu Glu Lys Glu Asp Phe Thr Arg Gly
                125                 130                 135

Lys Leu Met Ser Ser Leu His Leu Lys Arg Tyr Tyr Gly Arg Ile
                140                 145                 150

Leu His Tyr Leu Lys Ala Lys Glu Tyr Ser His Cys Ala Trp Thr
                155                 160                 165

Ile Val Arg Val Glu Ile Leu Arg Asn Phe Tyr Phe Ile Asn Arg
                170                 175                 180

Leu Thr Gly Tyr Leu Arg Asn 185         187

<210> SEQ ID NO 8
<211> LENGTH: 189
<212> TYPE: PRT
<213> ORGANISM: Homo sapiens

<400> SEQUENCE: 8

Met Ala Ser Pro Phe Ala Leu Leu Met Val Leu Val Val Leu Ser
 1               5                  10                  15

Cys Lys Ser Ser Cys Ser Leu Gly Cys Asp Leu Pro Glu Thr His
                20                  25                  30

Ser Leu Asp Asn Arg Arg Thr Leu Met Leu Leu Ala Gln Met Ser
                35                  40                  45

Arg Ile Ser Pro Ser Ser Cys Leu Met Asp Arg His Asp Phe Gly
                50                  55                  60

Phe Pro Gln Glu Glu Phe Asp Gly Asn Gln Phe Gln Lys Ala Pro
                65                  70                  75

Ala Ile Ser Val Leu His Glu Leu Ile Gln Gln Ile Phe Asn Leu
                80                  85                  90

Phe Thr Thr Lys Asp Ser Ser Ala Ala Trp Asp Glu Asp Leu Leu
                95                  100                 105

Asp Lys Phe Cys Thr Glu Leu Tyr Gln Gln Leu Asn Asp Leu Glu
                110                 115                 120

Ala Cys Val Met Gln Glu Glu Arg Val Gly Glu Thr Pro Leu Met
                125                 130                 135

Asn Ala Asp Ser Ile Leu Ala Val Lys Lys Tyr Phe Arg Arg Ile
                140                 145                 150

Thr Leu Tyr Leu Thr Glu Lys Lys Tyr Ser Pro Cys Ala Trp Glu
                155                 160                 165

Val Val Arg Ala Glu Ile Met Arg Ser Leu Ser Leu Ser Thr Asn
                170                 175                 180

Leu Gln Glu Arg Leu Arg Arg Lys Glu
                185         189

<210> SEQ ID NO 9
<211> LENGTH: 188
<212> TYPE: PRT
<213> ORGANISM: Homo sapiens

<400> SEQUENCE: 9

Met Ala Leu Thr Phe Ala Leu Leu Val Ala Leu Leu Val Leu Ser
 1               5                  10                  15

Cys Lys Ser Ser Cys Ser Val Gly Cys Asp Leu Pro Gln Thr His
                20                  25                  30

Ser Leu Gly Ser Arg Arg Thr Leu Met Leu Leu Ala Gln Met Arg
                35                  40                  45

Lys Ile Ser Leu Phe Ser Cys Leu Lys Asp Arg His Asp Phe Gly
                50                  55                  60

Phe Pro Gln Glu Glu Phe Gly Asn Gln Phe Gln Leu Ala Glu Thr
                65                  70                  75

Ile Pro Val Leu His Glu Met Ile Gln Gln Ile Phe Asn Leu Phe
                80                  85                  90

Ser Thr Leu Asp Ser Ser Ala Ala Trp Asp Glu Thr Leu Leu Asp
                95                  100                 105

Lys Phe Tyr Thr Glu Leu Tyr Gln Gln Leu Asn Asp Leu Glu Ala

-continued

```
                110                 115                 120
Cys Val Ile Gln Gly Val Gly Val Thr Glu Thr Pro Leu Met Lys
                125                 130                 135

Glu Asp Ser Ile Leu Ala Val Arg Lys Tyr Phe Gln Arg Ile Thr
                140                 145                 150

Leu Tyr Leu Lys Glu Lys Lys Tyr Ser Pro Cys Ala Trp Glu Val
                155                 160                 165

Val Arg Ala Glu Ile Met Arg Ser Phe Ser Leu Ser Thr Asn Leu
                170                 175                 180

Gln Glu Ser Leu Arg Ser Lys Glu
                185             188

<210> SEQ ID NO 10
<211> LENGTH: 189
<212> TYPE: PRT
<213> ORGANISM: Homo sapiens

<400> SEQUENCE: 10

Met Ala Leu Ser Phe Ser Leu Leu Met Ala Val Leu Val Leu Ser
  1               5                  10                  15

Tyr Lys Ser Ile Cys Ser Leu Gly Cys Asp Leu Pro Gln Thr His
                20                  25                  30

Ser Leu Gly Asn Arg Arg Ala Leu Ile Leu Leu Ala Gln Met Gly
                35                  40                  45

Arg Ile Ser His Phe Ser Cys Leu Lys Asp Arg His Asp Phe Gly
                50                  55                  60

Phe Pro Glu Glu Glu Phe Asp Gly His Gln Phe Gln Lys Thr Gln
                65                  70                  75

Ala Ile Ser Val Leu His Glu Met Ile Gln Gln Thr Phe Asn Leu
                80                  85                  90

Phe Ser Thr Glu Asp Ser Ser Ala Ala Trp Glu Gln Ser Leu Leu
                95                 100                 105

Glu Lys Phe Ser Thr Glu Leu Tyr Gln Gln Leu Asn Asp Leu Glu
                110                 115                 120

Ala Cys Val Ile Gln Glu Val Gly Val Glu Glu Thr Pro Leu Met
                125                 130                 135

Asn Val Asp Ser Ile Leu Ala Val Arg Lys Tyr Phe Gln Arg Ile
                140                 145                 150

Thr Leu Tyr Leu Thr Glu Lys Lys Tyr Ser Pro Cys Ala Trp Glu
                155                 160                 165

Val Val Arg Ala Glu Ile Met Arg Ser Leu Ser Phe Ser Thr Asn
                170                 175                 180

Leu Gln Lys Arg Leu Arg Arg Lys Asp
                185             189

<210> SEQ ID NO 11
<211> LENGTH: 189
<212> TYPE: PRT
<213> ORGANISM: Homo sapiens

<400> SEQUENCE: 11

Met Ala Leu Pro Phe Val Leu Leu Met Ala Leu Val Val Leu Asn
  1               5                  10                  15

Cys Lys Ser Ile Cys Ser Leu Gly Cys Asp Leu Pro Gln Thr His
                20                  25                  30

Ser Leu Ser Asn Arg Arg Thr Leu Met Ile Met Ala Gln Met Gly
```

-continued

```
                35                  40                  45
Arg Ile Ser Pro Phe Ser Cys Leu Lys Asp Arg His Asp Phe Gly
            50                  55                  60
Phe Pro Gln Glu Glu Phe Asp Gly Asn Gln Phe Gln Lys Ala Gln
            65                  70                  75
Ala Ile Ser Val Leu His Glu Met Ile Gln Gln Thr Phe Asn Leu
            80                  85                  90
Phe Ser Thr Lys Asp Ser Ser Ala Thr Trp Asp Glu Thr Leu Leu
            95                 100                 105
Asp Lys Phe Tyr Thr Glu Leu Tyr Gln Gln Leu Asn Asp Leu Glu
           110                 115                 120
Ala Cys Met Met Gln Glu Val Tyr Val Glu Asp Thr Pro Leu Met
           125                 130                 135
Asn Val Asp Ser Ile Leu Thr Val Arg Lys Tyr Phe Gln Arg Ile
           140                 145                 150
Thr Leu Tyr Leu Thr Glu Lys Lys Tyr Ser Pro Cys Ala Trp Glu
           155                 160                 165
Val Val Arg Ala Glu Ile Met Arg Ser Phe Ser Leu Ser Ala Asn
           170                 175                 180
Leu Gln Glu Arg Leu Arg Arg Lys Glu
           185                 189

<210> SEQ ID NO 12
<211> LENGTH: 189
<212> TYPE: PRT
<213> ORGANISM: Homo sapiens

<400> SEQUENCE: 12

Met Ala Leu Pro Phe Ala Leu Leu Met Ala Leu Val Val Leu Ser
  1               5                  10                  15
Cys Lys Ser Ser Cys Ser Leu Asp Cys Asp Leu Pro Gln Thr His
                 20                  25                  30
Ser Leu Gly His Arg Arg Thr Met Met Leu Leu Ala Gln Met Arg
                 35                  40                  45
Arg Ile Ser Leu Phe Ser Cys Leu Lys Asp Arg His Asp Phe Arg
             50                  55                  60
Phe Pro Gln Glu Glu Phe Asp Gly Asn Gln Phe Gln Lys Ala Glu
             65                  70                  75
Ala Ile Ser Val Leu His Glu Val Ile Gln Gln Thr Phe Asn Leu
             80                  85                  90
Phe Ser Thr Lys Asp Ser Ser Val Ala Trp Asp Glu Arg Leu Leu
             95                 100                 105
Asp Lys Leu Tyr Thr Glu Leu Tyr Gln Gln Leu Asn Asp Leu Glu
            110                 115                 120
Ala Cys Val Met Gln Glu Val Trp Val Gly Gly Thr Pro Leu Met
            125                 130                 135
Asn Glu Asp Ser Ile Leu Ala Val Arg Lys Tyr Phe Gln Arg Ile
            140                 145                 150
Thr Leu Tyr Leu Thr Glu Lys Lys Tyr Ser Pro Cys Ala Trp Glu
            155                 160                 165
Val Val Arg Ala Glu Ile Met Arg Ser Phe Ser Ser Ser Arg Asn
            170                 175                 180
Leu Gln Glu Arg Leu Arg Arg Lys Glu
            185                 189
```

```
<210> SEQ ID NO 13
<211> LENGTH: 189
<212> TYPE: PRT
<213> ORGANISM: Homo sapiens

<400> SEQUENCE: 13

Met Ala Arg Ser Phe Ser Leu Leu Met Val Val Leu Val Leu Ser
 1               5                  10                  15

Tyr Lys Ser Ile Cys Ser Leu Gly Cys Asp Leu Pro Gln Thr His
                20                  25                  30

Ser Leu Arg Asn Arg Arg Ala Leu Ile Leu Leu Ala Gln Met Gly
            35                  40                  45

Arg Ile Ser Pro Phe Ser Cys Leu Lys Asp Arg His Glu Phe Arg
            50                  55                  60

Phe Pro Glu Glu Glu Phe Asp Gly His Gln Phe Gln Lys Thr Gln
            65                  70                  75

Ala Ile Ser Val Leu His Glu Met Ile Gln Gln Thr Phe Asn Leu
            80                  85                  90

Phe Ser Thr Glu Asp Ser Ser Ala Ala Trp Glu Gln Ser Leu Leu
            95                  100                 105

Glu Lys Phe Ser Thr Glu Leu Tyr Gln Gln Leu Asn Asp Leu Glu
            110                 115                 120

Ala Cys Val Ile Gln Glu Val Gly Val Glu Glu Thr Pro Leu Met
            125                 130                 135

Asn Glu Asp Phe Ile Leu Ala Val Arg Lys Tyr Phe Gln Arg Ile
            140                 145                 150

Thr Leu Tyr Leu Met Glu Lys Lys Tyr Ser Pro Cys Ala Trp Glu
            155                 160                 165

Val Val Arg Ala Glu Ile Met Arg Ser Phe Ser Phe Ser Thr Asn
            170                 175                 180

Leu Lys Lys Gly Leu Arg Arg Lys Asp
            185                 189

<210> SEQ ID NO 14
<211> LENGTH: 189
<212> TYPE: PRT
<213> ORGANISM: Homo sapiens

<400> SEQUENCE: 14

Met Ala Leu Thr Phe Tyr Leu Leu Val Ala Leu Val Val Leu Ser
 1               5                  10                  15

Tyr Lys Ser Phe Ser Ser Leu Gly Cys Asp Leu Pro Gln Thr His
                20                  25                  30

Ser Leu Gly Asn Arg Arg Ala Leu Ile Leu Leu Ala Gln Met Arg
            35                  40                  45

Arg Ile Ser Pro Phe Ser Cys Leu Lys Asp Arg His Asp Phe Glu
            50                  55                  60

Phe Pro Gln Glu Glu Phe Asp Asp Lys Gln Phe Gln Lys Ala Gln
            65                  70                  75

Ala Ile Ser Val Leu His Glu Met Ile Gln Gln Thr Phe Asn Leu
            80                  85                  90

Phe Ser Thr Lys Asp Ser Ser Ala Ala Leu Asp Glu Thr Leu Leu
            95                  100                 105

Asp Glu Phe Tyr Ile Glu Leu Asp Gln Gln Leu Asn Asp Leu Glu
            110                 115                 120
```

Ser Cys Val Met Gln Glu Val Gly Val Ile Glu Ser Pro Leu Met
            125                 130                 135

Tyr Glu Asp Ser Ile Leu Ala Val Arg Lys Tyr Phe Gln Arg Ile
            140                 145                 150

Thr Leu Tyr Leu Thr Glu Lys Lys Tyr Ser Ser Cys Ala Trp Glu
            155                 160                 165

Val Val Arg Ala Glu Ile Met Arg Ser Phe Ser Leu Ser Ile Asn
            170                 175                 180

Leu Gln Lys Arg Leu Lys Ser Lys Glu
            185             189

<210> SEQ ID NO 15
<211> LENGTH: 189
<212> TYPE: PRT
<213> ORGANISM: Homo sapiens

<400> SEQUENCE: 15

Met Ala Leu Ser Phe Ser Leu Leu Met Ala Val Leu Val Leu Ser
 1               5                  10                  15

Tyr Lys Ser Ile Cys Ser Leu Gly Cys Asp Leu Pro Gln Thr His
            20                  25                  30

Ser Leu Gly Asn Arg Arg Ala Leu Ile Leu Leu Gly Gln Met Gly
            35                  40                  45

Arg Ile Ser Pro Phe Ser Cys Leu Lys Asp Arg His Asp Phe Arg
            50                  55                  60

Ile Pro Gln Glu Glu Phe Asp Gly Asn Gln Phe Gln Lys Ala Gln
            65                  70                  75

Ala Ile Ser Val Leu His Glu Met Ile Gln Gln Thr Phe Asn Leu
            80                  85                  90

Phe Ser Thr Glu Asp Ser Ser Ala Ala Trp Glu Gln Ser Leu Leu
            95                  100                 105

Glu Lys Phe Ser Thr Glu Leu Tyr Gln Gln Leu Asn Asp Leu Glu
            110                 115                 120

Ala Cys Val Ile Gln Glu Val Gly Val Glu Glu Thr Pro Leu Met
            125                 130                 135

Asn Glu Asp Ser Ile Leu Ala Val Arg Lys Tyr Phe Gln Arg Ile
            140                 145                 150

Thr Leu Tyr Leu Ile Glu Arg Lys Tyr Ser Pro Cys Ala Trp Glu
            155                 160                 165

Val Val Arg Ala Glu Ile Met Arg Ser Leu Ser Phe Ser Thr Asn
            170                 175                 180

Leu Gln Lys Arg Leu Arg Arg Lys Asp
            185             189

<210> SEQ ID NO 16
<211> LENGTH: 189
<212> TYPE: PRT
<213> ORGANISM: Homo sapiens

<400> SEQUENCE: 16

Met Ala Leu Pro Phe Ala Leu Met Met Ala Leu Val Val Leu Ser
 1               5                  10                  15

Cys Lys Ser Ser Cys Ser Leu Gly Cys Asn Leu Ser Gln Thr His
            20                  25                  30

Ser Leu Asn Asn Arg Arg Thr Leu Met Leu Met Ala Gln Met Arg
            35                  40                  45

```
Arg Ile Ser Pro Phe Ser Cys Leu Lys Asp Arg His Asp Phe Glu
             50                  55                  60

Phe Pro Gln Glu Glu Phe Asp Gly Asn Gln Phe Gln Lys Ala Gln
             65                  70                  75

Ala Ile Ser Val Leu His Glu Met Met Gln Gln Thr Phe Asn Leu
             80                  85                  90

Phe Ser Thr Lys Asn Ser Ser Ala Ala Trp Asp Glu Thr Leu Leu
             95                 100                 105

Glu Lys Phe Tyr Ile Glu Leu Phe Gln Gln Met Asn Asp Leu Glu
            110                 115                 120

Ala Cys Val Ile Gln Glu Val Gly Val Glu Glu Thr Pro Leu Met
            125                 130                 135

Asn Glu Asp Ser Ile Leu Ala Val Lys Lys Tyr Phe Gln Arg Ile
            140                 145                 150

Thr Leu Tyr Leu Met Glu Lys Lys Tyr Ser Pro Cys Ala Trp Glu
            155                 160                 165

Val Val Arg Ala Glu Ile Met Arg Ser Leu Ser Phe Ser Thr Asn
            170                 175                 180

Leu Gln Lys Arg Leu Arg Arg Lys Asp
            185                 189

<210> SEQ ID NO 17
<211> LENGTH: 189
<212> TYPE: PRT
<213> ORGANISM: Homo sapiens

<400> SEQUENCE: 17

Met Ala Leu Ser Phe Ser Leu Leu Met Ala Val Leu Val Leu Ser
  1              5                  10                  15

Tyr Lys Ser Ile Cys Ser Leu Gly Cys Asp Leu Pro Gln Thr His
             20                  25                  30

Ser Leu Gly Asn Arg Arg Ala Leu Ile Leu Leu Ala Gln Met Gly
             35                  40                  45

Arg Ile Ser His Phe Ser Cys Leu Lys Asp Arg Tyr Asp Phe Gly
             50                  55                  60

Phe Pro Gln Glu Val Phe Asp Gly Asn Gln Phe Gln Lys Ala Gln
             65                  70                  75

Ala Ile Ser Ala Phe His Glu Met Ile Gln Gln Thr Phe Asn Leu
             80                  85                  90

Phe Ser Thr Lys Asp Ser Ser Ala Ala Trp Asp Glu Thr Leu Leu
             95                 100                 105

Asp Lys Phe Tyr Ile Glu Leu Phe Gln Gln Leu Asn Asp Leu Glu
            110                 115                 120

Ala Cys Val Thr Gln Glu Val Gly Val Glu Glu Ile Ala Leu Met
            125                 130                 135

Asn Glu Asp Ser Ile Leu Ala Val Arg Lys Tyr Phe Gln Arg Ile
            140                 145                 150

Thr Leu Tyr Leu Met Gly Lys Lys Tyr Ser Pro Cys Ala Trp Glu
            155                 160                 165

Val Val Arg Ala Glu Ile Met Arg Ser Phe Ser Phe Ser Thr Asn
            170                 175                 180

Leu Gln Lys Gly Leu Arg Arg Lys Asp
            185                 189

<210> SEQ ID NO 18
```

```
<211> LENGTH: 189
<212> TYPE: PRT
<213> ORGANISM: Homo sapiens

<400> SEQUENCE: 18

Met Ala Leu Ser Phe Ser Leu Leu Met Ala Val Leu Val Leu Ser
 1               5                  10                  15

Tyr Lys Ser Ile Cys Ser Leu Gly Cys Asp Leu Pro Gln Thr His
                20                  25                  30

Ser Leu Gly Asn Arg Arg Ala Leu Ile Leu Leu Ala Gln Met Gly
                35                  40                  45

Arg Ile Ser Pro Phe Ser Cys Leu Lys Asp Arg His Asp Phe Gly
                50                  55                  60

Leu Pro Gln Glu Glu Phe Asp Gly Asn Gln Phe Gln Lys Thr Gln
                65                  70                  75

Ala Ile Ser Val Leu His Glu Met Ile Gln Gln Thr Phe Asn Leu
                80                  85                  90

Phe Ser Thr Glu Asp Ser Ser Ala Ala Trp Glu Gln Ser Leu Leu
                95                 100                 105

Glu Lys Phe Ser Thr Glu Leu Tyr Gln Gln Leu Asn Asn Leu Glu
               110                 115                 120

Ala Cys Val Ile Gln Glu Val Gly Met Glu Glu Thr Pro Leu Met
               125                 130                 135

Asn Glu Asp Ser Ile Leu Ala Val Arg Lys Tyr Phe Gln Arg Ile
               140                 145                 150

Thr Leu Tyr Leu Thr Glu Lys Lys Tyr Ser Pro Cys Ala Trp Glu
               155                 160                 165

Val Val Arg Ala Glu Ile Met Arg Ser Leu Ser Phe Ser Thr Asn
               170                 175                 180

Leu Gln Lys Ile Leu Arg Arg Lys Asp
               185                 189

<210> SEQ ID NO 19
<211> LENGTH: 189
<212> TYPE: PRT
<213> ORGANISM: Homo sapiens

<400> SEQUENCE: 19

Met Ala Leu Ser Phe Ser Leu Leu Met Ala Val Leu Val Leu Ser
 1               5                  10                  15

Tyr Lys Ser Ile Cys Ser Leu Gly Cys Asp Leu Pro Gln Thr His
                20                  25                  30

Ser Leu Gly Asn Arg Arg Ala Leu Ile Leu Leu Ala Gln Met Gly
                35                  40                  45

Arg Ile Ser Pro Phe Ser Cys Leu Lys Asp Arg His Asp Phe Gly
                50                  55                  60

Phe Pro Gln Glu Glu Phe Asp Gly Asn Gln Phe Gln Lys Ala Gln
                65                  70                  75

Ala Ile Ser Val Leu His Glu Met Ile Gln Gln Thr Phe Asn Leu
                80                  85                  90

Phe Ser Thr Lys Asp Ser Ser Ala Thr Trp Glu Gln Ser Leu Leu
                95                 100                 105

Glu Lys Phe Ser Thr Glu Leu Asn Gln Gln Leu Asn Asp Met Glu
               110                 115                 120

Ala Cys Val Ile Gln Glu Val Gly Val Glu Glu Thr Pro Leu Met
               125                 130                 135
```

-continued

```
Asn Val Asp Ser Ile Leu Ala Val Lys Lys Tyr Phe Gln Arg Ile
            140                 145                 150

Thr Leu Tyr Leu Thr Glu Lys Lys Tyr Ser Pro Cys Ala Trp Glu
            155                 160                 165

Val Val Arg Ala Glu Ile Met Arg Ser Phe Ser Leu Ser Lys Ile
            170                 175                 180

Phe Gln Glu Arg Leu Arg Arg Lys Glu
            185             189
```

```
<210> SEQ ID NO 20
<211> LENGTH: 276
<212> TYPE: DNA
<213> ORGANISM: Homo sapiens
<220> FEATURE:
<221> NAME/KEY: unsure
<222> LOCATION: 163
<223> OTHER INFORMATION: n may be any nucleotide

<400> SEQUENCE: 20
aaactttctg cttcctcaga agtctttgag tcctcagcag taccaaaaag         50
gacacactct ggccattctc catgagatgc ttcagcagat cttcagcctc        100
ttcagggcaa atatttctct ggatggttgg gaggaaaacc acacggagaa        150
attcttcatt cancttcatc aacagctaga ataccctagaa gcactcatgg       200 gactggaagc agagaagcta agtggtactt tgggtagtga taaccttaga       250
ttacaagtta aaatgtactt ccgaag                                  276
```

```
<210> SEQ ID NO 21
<211> LENGTH: 276
<212> TYPE: DNA
<213> ORGANISM: Homo sapiens
<220> FEATURE:
<221> NAME/KEY: unsure
<222> LOCATION: 114
<223> OTHER INFORMATION: n may be any nucleotide.

<400> SEQUENCE: 21
cttcggaagt acattttaac ttgtaatcta aggttatcac tacccaaagt         50
accacttagc ttctctgctt ccagtcccat gagtgcttct aggtattcta        100
gctgttgatg aagntgaatg aggaatttct ccgtgtggtt ttcctcccaa        150
ccatccagag aaatatttgc cctgaagagg ctgaagatct gctgaagcat        200
ctcatggaga atggccagag tgtgtccttt ttggtactgc tgaggactca        250
aagacttctg aggaagcaga aagttt                                  276
```

```
<210> SEQ ID NO 22
<211> LENGTH: 91
<212> TYPE: PRT
<213> ORGANISM: Homo sapiens
<220> FEATURE:
<221> NAME/KEY: unsure
<222> LOCATION: 54
<223> OTHER INFORMATION: Xaa may be any amino acid.

<400> SEQUENCE: 22

Asn Phe Leu Leu Pro Gln Lys Ser Leu Ser Pro Gln Gln Tyr Gln
 1               5                  10                  15

Lys Gly His Thr Leu Ala Ile Leu His Glu Met Leu Gln Gln Ile
            20                  25                  30
```

-continued

```
Phe Ser Leu Phe Arg Ala Asn Ile Ser Leu Asp Gly Trp Glu Glu
                35                  40                  45

Asn His Thr Glu Lys Phe Leu Ile Xaa Leu His Gln Gln Leu Glu
                50                  55                  60

Tyr Leu Glu Ala Leu Met Gly Leu Glu Ala Glu Lys Leu Ser Gly
                65                  70                  75

Thr Leu Gly Ser Asp Asn Leu Arg Leu Gln Val Lys Met Tyr Phe
                80                  85                  90

Arg
 91
```

What is claimed is:

1. An isolated nucleic acid molecule having at least a 95% sequence identity to (a) a DNA molecule encoding a novel human interferon polypeptide designated PRO655 comprising the sequence of amino acids from about 22 to 189 of FIG. 1 (SEQ ID NO: 1), or (b) the complement of the DNA molecule of (a).

2. The isolated nucleic acid molecule of claim 1 having at least 95% sequence identity to (a) a DNA molecule encoding a PRO655 polypeptide comprising the sequence of amino acids 22 to 208 of FIG. 1 (SEQ ID NO: 1), or (b) the complement of the DNA molecule of (a).

3. The isolated nucleic acid molecule of claim 1 having at least 95% sequence identity to (a) a DNA molecule encoding a PRO655 polypeptide comprising the sequence of amino acids 1 to 208 of FIG. 1 (SEQ ID NO: 1), or the complement of the DNA molecule of (a).

4. An isolated nucleic acid molecule having at least a 95% sequence identity to (a) a DNA molecule encoding the same mature polypeptide encoded by the human interferon cDNA in ATCC Deposit No. 209509 (DNA50960-1224), or (b) the complement of the DNA molecule of (a).

5. A vector comprising the nucleic acid molecule of claim 1.

6. The vector of claim 5 operably linked to control sequences recognized by a host cell transformed with the vector.

7. A host cell comprising the vector of claim 5.

8. The host cell of claim 7 wherein said cell is a CHO cell.

9. The host cell of claim 7 wherein said cell is an *E. coli*.

10. The host cell of claim 7 wherein said cell is a yeast cell.

11. A process for producing PRO655 polypeptides comprising culturing the host cell of claim 7 under conditions suitable for expression of PRO655 and recovering PRO655 from the cell culture.

12. An isolated PRO655 polypeptide comprising a sequence having at least 95% amino acid sequence identity with the sequence of amino acids from about 22 to 189 of FIG. 1 (SEQ ID NO:1).

13. A chimeric molecule comprising the PRO655 polypeptide as in claim 12 fused to a heterologous amino acid sequence.

14. The chimeric molecule of claim 13 wherein said heterologous amino acid sequence is an epitope tag sequence.

15. The chimeric molecule of claim 13 wherein said heterologous amino acid sequence is a Fc region of an immunoglobulin.

* * * * *